United States Patent
Nickisch et al.

(10) Patent No.: US 10,111,633 B2
(45) Date of Patent: Oct. 30, 2018

(54) LOCAL FFR ESTIMATION AND VISUALISATION FOR IMPROVED FUNCTIONAL STENOSIS ANALYSIS

(71) Applicant: KONINKLIJKE PHILIPS N.V., Eindhoven (NL)

(72) Inventors: Hannes Nickisch, Hamburg (DE); Michael Grass, Hamburg (DE); Holger Schmitt, Hamburg (DE); Jan Timmer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 11 days.

(21) Appl. No.: 15/101,025

(22) PCT Filed: Dec. 4, 2014

(86) PCT No.: PCT/EP2014/076477
§ 371 (c)(1),
(2) Date: Jun. 2, 2016

(87) PCT Pub. No.: WO2015/082576
PCT Pub. Date: Jun. 11, 2015

(65) Prior Publication Data
US 2016/0302750 A1 Oct. 20, 2016

(30) Foreign Application Priority Data
Dec. 4, 2013 (EP) ..................................... 13195675

(51) Int. Cl.
*G06K 9/00* (2006.01)
*A61B 6/00* (2006.01)
(Continued)

(52) U.S. Cl.
CPC .......... *A61B 6/507* (2013.01); *A61B 5/02007* (2013.01); *A61B 5/02028* (2013.01);
(Continued)

(58) Field of Classification Search
None
See application file for complete search history.

(56) References Cited

U.S. PATENT DOCUMENTS 8,315,813 B2 * 11/2012 Taylor ................ A61B 5/02007 702/19
8,734,357 B2 * 5/2014 Taylor ................ A61B 5/02007 600/504
(Continued)

FOREIGN PATENT DOCUMENTS

WO 2013171644 A1 11/2013

OTHER PUBLICATIONS

Abbott, J. Dawn, "The Use of Fractional Row Reserve in Serial Stenoses", JACC: Cardiovascular Interventions, vol. 5, No. 10, 2012.
(Continued)

*Primary Examiner* — Nancy Bitar

(57) ABSTRACT

A system (IPS) and related method for fractional flow reserve, FFR, simulation. The simulation for a range of FFR values for a vasculature portion is based on a composite transfer function which is combined from a weighted sum of global effect transfer functions he, each representing a distinct physical effect that causes a pressure drop. The weights we are gotten from a previous training phase against pressure pi versus flow rate fi 5 sample measurements associated with respective vasculature geometries. The simulated range of FFR values is visualized in a graphics display (GD) as a function of pressure and flow rate values within respective intervals.

8 Claims, 6 Drawing Sheets

(51) Int. Cl.
*A61B 5/00* (2006.01)
*A61B 5/02* (2006.01)
*G06T 7/00* (2017.01)
*G16H 50/50* (2018.01)
*G06F 19/00* (2018.01)
*A61B 5/026* (2006.01)
*A61B 6/03* (2006.01)

(52) U.S. Cl.
CPC ............ *A61B 5/742* (2013.01); *A61B 6/4441* (2013.01); *A61B 6/463* (2013.01); *A61B 6/504* (2013.01); *A61B 6/5217* (2013.01); *G06F 19/00* (2013.01); *G06T 7/0012* (2013.01); *G16H 50/50* (2018.01); *A61B 5/026* (2013.01); *A61B 6/032* (2013.01); *A61B 6/481* (2013.01); *G06T 2207/10072* (2013.01); *G06T 2207/10081* (2013.01); *G06T 2207/10121* (2013.01); *G06T 2207/20081* (2013.01); *G06T 2207/30104* (2013.01); *G06T 2207/30172* (2013.01)

(56) References Cited

U.S. PATENT DOCUMENTS

| | | | |
|---|---|---|---|
| 2012/0041318 A1* | 2/2012 | Taylor | A61B 5/02 600/504 |
| 2013/0132054 A1 | 5/2013 | Sharma | |
| 2013/0226003 A1 | 8/2013 | Edie | |
| 2013/0246034 A1* | 9/2013 | Sharma | G06F 19/12 703/11 |
| 2014/0161766 A1* | 6/2014 | Chang | A61K 39/395 424/85.2 |
| 2015/0297161 A1* | 10/2015 | Grass | A61B 6/503 600/426 |

OTHER PUBLICATIONS

Bernhard, Stefan et al "Transient Integral boundary layer method to calculate the transleslonal pressure drop and the fractional flow reserve in myocardial bridges", Biomedical Engineering Online, 2006.

De Bruyne, Bernard et al "Pressure-Derived Fractional Flow Reserve to Assess Serial Epicardial Stenoses Theoretical Basis and Animal Validation", Circulation, 2000.

Huo, Yunlong et al "A validated predictive model of coronary fractional flow reserve", J.R. Soc. Inteface, vol. 9, pp. 1325-1338, 2012.

Al-Hassan, Donya et al "Noninvasive fractional flow reserve derived from coronary computed tomography angiography: integrated anatomical and functional assessment", Future Cardiology, vol. 9, No. 2, pp. 243-251, 2013.

Tar, B. et al "The Effect of the Sensor Position of the Pressure Wire Distal to a Coronary Stenosis on the Calculated Fractional Flow Reserve", Computing in Cardiology, 2013, vol. 40, pp. 1099-1102.

Gould, K Lance et al "Experimental Validation of Quantitative Coronary Arteriography for Determining Pressure-Flow Characteristics of Coronary Stenosis", Circulation, vol. 66, No. 5, 1982, pp. 930-937.

* cited by examiner

| Effect | Degree | Local Coefficient | Local geometry |
|---|---|---|---|
| Bernoulli | $d=2$ | $\alpha_B = \frac{\varrho}{2}(1/A_{out}^2 - 1/A_{in}^2)$ | |
| Bifurcation | $d=2$ | $\alpha_S = \frac{\varrho}{2}(1/(A_1+A_2)^2 - 1/A_{in}^2)$ | |
| Poiseuille Friction | $d=1$ | $\alpha_P = \frac{8\pi\mu l}{A^2}$ | |
| Curvature | $d=1$ | $\alpha_C = \alpha_P(\frac{19}{8}(r\kappa)^{0.15}-1)$ | |
| Ovality | $d=1$ | $\alpha_O = \alpha_P(r/r_H)^4, r_H = 2A/P$ | |
| Expansion Borda-Carnot | $d=2$ | $\alpha_E = \frac{\varrho}{2}\max^2(0, 1/A_{in} - 1/A_{out})$ | |

Fig.6

LOCAL FFR ESTIMATION AND VISUALISATION FOR IMPROVED FUNCTIONAL STENOSIS ANALYSIS

CROSS REFERENCE TO PRIOR APPLICATIONS

This application is the U.S. National Phase application under 35 U.S.C. § 371 of International Application No. PCT/EP2014/076477, filed on Dec. 4, 2014, which claims the benefit of European Patent Application No. 13195675.7, filed Dec. 4, 2013. These applications are hereby incorporated by reference herein.

FIELD OF THE INVENTION

The invention relates to an image processing method, to an image processing system, to a computer program element, and to a computer readable medium.

BACKGROUND OF THE INVENTION

Societies around the world are much inflicted by cardiovascular diseases. Cardiovascular diseases are still among the leading causes of deaths worldwide. Lack of exercise, unhealthy diet and other factors may lead for instance to stenoses, a condition where part of the cardio vasculature is constricted. The strictures may cause undersupply of tissue downstream the stenosis. Although treatments of stenoses are available, these are largely interventional and are not without risks. For instance, one interventional procedure is the introduction of a stent into the vasculature via a catheter. The stent is then navigated to the stenosed site and made to expand there in order to enlarge and so restore lost vessel cross-section. But these types of interventional treatments are not without risk and they put strain on already cash-strapped national health services—sometimes even unnecessarily. For instance, if a stricture occurs in a part of vessel that supplies already moribund tissue, it is questionable whether the intervention will actually result in any positive health effects. The moribund tissue cannot be revived and the blood flow, limited as it may be because of the stricture, may still be just enough in some cases. The technique of FFR (fractional flow reserve) determination comes to the aid here as it allows assessing the severity of the stenosis in terms of a score, that is, a number. FFR is a measure of stenosis' severity besides coronary artery geometry, because it includes the impact of the stenosis on blood flow. The clinical relevance of invasive FFR measurements during catheterization procedures has been proven in clinical studies. Medical staff can then better judge whether an intervention is warranted in the circumstances. One way to establish this number is to take in-situ measurements that include differential pressure across the stenosed site and blood flow rate therethrough. A special catheter is used for this that is equipped with suitable probes to take the measurements. The catheter is placed distal and then proximal to the stenosed site to establish in particular the pressure differential. But again, this is not without risk either as the catheter will need to be forced through the stenosed site. Also, the interventional tool itself is complex and expensive to procure and there usually is the need to administer potentially harmful substances such as Adenosine to increase hyperemia in the cardio region.

Therefore non-invasive local FFR estimation methods for catheterization lab application have been proposed in the past to avoid the use of expensive in-situ pressure measurement equipment. A variant of these methods is based on volumetric data reconstructed from CT projections. Another variant of this method is in general based on volumetric models of the coronary arteries generated from a set of angiographic projections (3D coronary angiography (3DCA)). Both variants are based on computational fluid dynamics (CFD) simulations.

These known methods were observed to be at times computationally expensive and/or tend to incur relatively high dosage for the patient.

SUMMARY OF THE INVENTION

There may therefore be a need for an alternative way of determining fractional flow reserve values more efficiently and less burdensome for the patient.

The object of the present invention is solved by the subject matter of the independent claims where further embodiments are incorporated in the dependent claims. It should be noted that the following described aspect of the invention equally apply to the image processing method, to the computer program element and to the computer readable medium According to a first aspect of the invention there is provided an image processing system, comprising:

an input port for receiving at least one image including a projection view of an object of interest;

a segmenter configured to segment the image to obtain an object segmentation for the object as per the projection view;

a partitioner configured to partition the segmentation into components;

an adaptation unit configured to adapt one or more of a plurality of local effect transfer functions to the local geometry of the object as recorded in respective ones of the components to obtain a plurality of global effect transfer functions;

a combiner configured to combine the plurality of global effect transfer functions into a composite transfer function for the object;

an evaluator configured to compute from the composite transfer function an FFR estimate for a fluid flowing through the object.

For instance, when using the proposed system to simulate FFR for a relevant part of the coronaries around the stenosed site, the local effect transfer function describes local pressure drops attributable to a specific physical effect essentially in isolation whereas the global effect transfer function describes the pressure drops caused by the respective effect across the whole of the imaged vessel tree or at least over the whole of a region of interest around the stenosis. The composite transfer function then describes the overall pressure drop across the object whilst accounting for correlations and interactions between the various effects. In other words, a "lumped" parameter model is proposed, herein defined by geometry-derived transfer functions are used for the simulation of the fluid behavior under consideration, for instance, in one embodiment, human or animal blood circulation.

According to one embodiment, the evaluator is configured to compute a range of FFR estimates by varying at least one physical or physiological parameter.

In other words the evaluator samples the FFR surface as defined by the functional relation between the physical or physiological parameters.

According to one embodiment, the image processing system further comprises a visualizer configured to render for display on a display unit the range of FFR estimates as a function of the at least one physical or physiological parameter. In one embodiment, the range of FFR estimates in their functional dependence can then be displayed on a display unit. Visualizing the FFR values for a range of physiological conditions in the vessel allows accounting for the fact that the anatomical knowledge to estimate the boundary conditions for the FFR computation is limited to make the calculation simpler and hence quicker.

According to one embodiment, the parameter is at least one of a pressure and a flow rate and wherein the range of FFR estimates is displayed as a function of at least one of pressure and flow rate. The displayed FFR estimation may also be based on varying other variables/parameters that were used to compute the FFR. For instance, in some embodiments, any one of (or any combination of the following) may be varied instead or in addition to flow/pressure variations: the hematocrit level, blood viscosity, or blood density. In one embodiment, the user can select which variables are to be varied.

According to one embodiment, the local effect transfer functions are linearly combined using weights previously learned from pressure versus flow rate sample measurements/simulations. In other words, the invention harnesses a data corpus of previous in-situ pressure/flow measurements and/or coronary CFD computations to learn the relative contributions (measured by said weights) of the various physical effects (for instance Bernoulli and/or (Poiseuille) friction, etc.) to the overall or net pressure drop across the coronaries. After training the weights to a sufficiently large data corpus, the proposed system is ready for use. The need to conduct in-situ measurements and/or to run computationally expensive CFD simulations for future FFR simulation is avoided when using the proposed system.

According to one embodiment, the image is acquired by a planar X-ray apparatus of the C-arm type. In particular there is no need to feed the proposed apparatus with reconstructed CT volumetric imagery. A few discrete angular samples of projection views are sufficient although the more projections from different projections are used the better the fidelity of the simulation. The adaptation is based in one embodiment on the geometry as summarized by a 3D vessel centerline and the CSAs (cross sectional areas), both can be generated for instance from a rotational X-ray acquisition (circular or otherwise) from one or multiple 2D angiograms acquired along different viewing angles. A number of different imaging modalities for acquisition of the projection images are envisaged herein, for instance CT, rotational C-arm, MRI and others. Phase-contrast imaging or spectral images are also envisaged herein. In one embodiment, phase-contrast imaging is used without contrast agent injection.

Although the proposed methods may be used to harnesses previous in-situ (that is, interventional) pressure measurements to train the weights used to combine the composite function, there is no longer reliance on or necessity for interventions for pressure measure purposes once the weights are gotten although such in-situ pressure measurements may still be used herein. In other words, no coronary intervention for taking pressure measurements is required to obtain FFR information for given patient.

The proposed system allows generating virtual FFR information in the CathLab (catheterization laboratory) using the 3D information about the vascular geometry and to present said information to the interventional cardiologist.

Also, it has been observed that CT coronary angiography (CTCA) and CFD rely on error prone estimates for an extensive set of boundary conditions. For instance, CTCA based virtual FFR requires boundary conditions at the inflow or outflow of the vascular system being evaluated. But boundary conditions related to the myocardial muscle that supplies the pressure for vascular system are difficult to estimate. Therefore, the relatively fast calculation of the set of FFR values for a range of boundary conditions as proposed herein in one embodiment can be advantageous. Also, no administration of hyperemia maximizing substances is needed.

Although in one embodiment the proposed system is used in FFR simulation to investigate blood flow behavior in stenosed coronaries, the system may be also used with benefit in respect of other parts of the human (or animal) vasculature. Also, the system's use is not restricted to medical context. For instance, examination of inaccessible, complex plumbing systems in civil engineering or of hydraulic pipe networks in production facilities or vehicles (such as aircraft or ships) are also envisaged herein.

BRIEF DESCRIPTION OF THE DRAWINGS

Exemplary embodiments of the invention will now be described with reference to the following drawings wherein:

FIG. 6 shows a table of geometry dependent parameterizations for adapting local transfer functions.

DETAILED DESCRIPTION OF EMBODIMENTS

Figure 1:
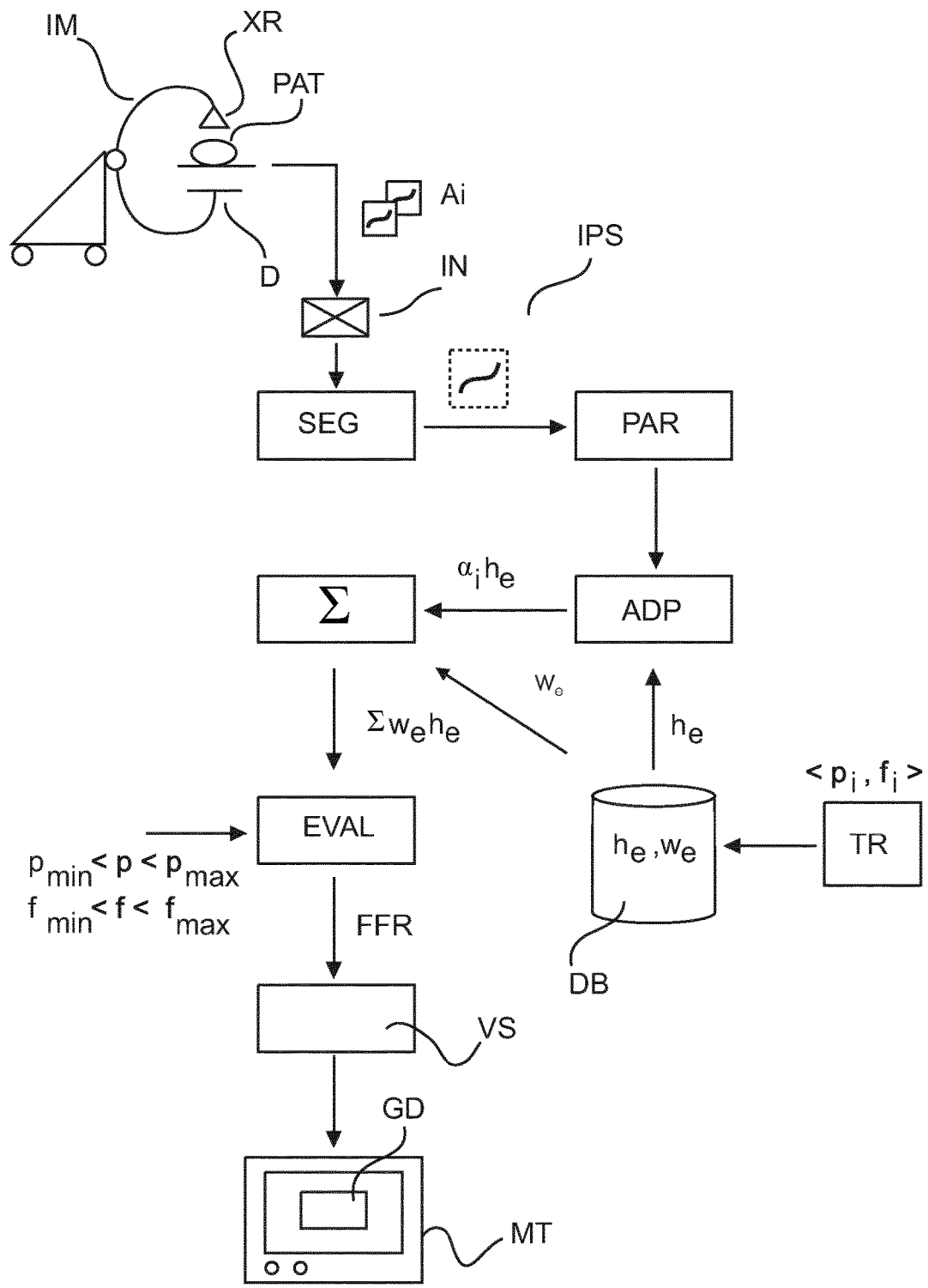
FIG. 1 shows a schematic block diagram of an image processing system for simulating FFR information.

With reference to FIG. 1, there is shown an image processing system IPS that allows FFR simulation. The system allows computing FFR values from images Ai that encode image contrast sufficient to identify respective projection views ("footprints") of the coronaries in form of a vessel tree of a patient PAT.

The imagery Ai is acquired by an imager IM, for instance, a planar X-ray radiography apparatus or a rotational X-ray C-arm system or other suitable imaging modality. The imager IM includes an X-ray source XR and detector D. The patient is exposed at the relevant region of interest (for instance the cardio region) to radiation that emanates from the X-ray source XR. The radiation interacts with matter in the region of interest (in this case the cardio region) and is then detected at the detector D. The radiation detected at the detector D is translated into said digital images Ai which are output and received by the image processing system IPS at its input port IN.

In one embodiment, the imager IM supplying imagery Ai is a C-arm X-ray fluoroscopy system. Although in principle the FFR simulation may be based on a single image Ai acquired of the coronary of interest, it is a preferred embodiment to use at least two images (in some embodiments, exactly 2 images). In one embodiment a bi-plane X-ray C-arm system is used and the two images A1,A2 are acquired at different (for instance orthogonal) projection directions and such an image pair A1,A2 has been found to supply enough image information on the 3D structure of a vessel tree for present purposes. Because of the low radiation absorption property of vasculature tissue, the images are in one embodiment angiograms, that is, they are X-ray images acquired whilst a contrast agent was resident in the patient's vasculature. This is but one embodiment however, as the use of imagers with phase contrast imaging capable equipment, is also envisaged herein as these types of imaging systems are capable of providing in some instances sufficient contrast even though there is no contrast agent resident in the vasculature. In one embodiment, phase contrast imagers include a series of interferometric gratings arranged between the x-ray tube and detector D.

Broadly, the present system IPS affords computing FFR values for a specific patient without taking, at the time of the computations or simulations, in situ pressure measurements and without running extensive CFD simulations. In contrast to these approaches, the system uses a data corpus of measurements that have been taken in the past. More particularly, a training module TR harnesses this knowledge in form of blood flow versus pressure drop sample pairs $<f_i, \Delta p_i>$. A set of weights $w_e$ is learned from this data corpus. The weights $w_e$ can be used to "compose" a composite transfer function by combining a plurality of locally adapted local effects transfer functions or basis function templates. Each local effect transfer function represents, in isolation, a different, individual physical effect that would each cause a certain pressure drop. Templates of those basis functions are held in a library or database DB and are adapted to the image information in the received images A1, A2 of the actual patient. Individual physical effects that have hitherto been considered only separately are now considered in combination in order to better model various interactions between those effects. This allows arriving at the composite transfer function that has been found to afford remarkably realistic modeling of the fluid dynamics around the stenosed area at reasonable computational cost. The proposed system has been found to be highly responsive because of the relative simplicity of the present system as compared to computationally expensive CFD. The FFR estimates are delivered in nearly real-time as the images are processed to identify (for instance via segmentation) the vessel tree which is a benefit in busy cath lab environments where quick decisions on whether or not to conduct the intervention are called for. After adaptation or "tailoring" the composite function to the image information for the instant patient, the composite function is used to compute a range of FFR values which are then visualized by a visualizer VS on screen MT in order to better cope with the remaining uncertainties and to thereby furnish to the user a realistic high fidelity picture of the FFR situation at the stenosed site. The physician can then better assess the severity of the stenosis. Operation of the image processing system will now be explained in more detail. The first part of the following description will concentrate on the computational aspects and the second part will center around the visualization aspect.

The following summarizes the use of different imaging modalities in different embodiments to acquired one or more projection images. A mentioned above, in one embodiment, angiographic projection(s) are generated via a local contrast injection with a catheter.

According to one embodiment, a single angiographic projection is acquired by a planar X-ray imager.

According to an alternative embodiment, a bi-plane system with a single contrast bolus is used to acquire two projections at the same point in time which allow generating a more accurate 3D vessel model.

According to an alternative embodiment, a single plane C-arm system with two acquisitions and two or more contrast injections is used to generate a more accurate model from different projections. In one embodiment, one acquires an ECG (electro-cardiogram) in parallel to combine projections of the same cardiac phase.

One can use a single-plane C-arm system with a single contrast injection and operate the C-arm system to obtain rotational acquisitions and then select angiograms from this sequence which correspond in ECG phase to arrive at different acquisition angles to generate a more accurate model tree vessel model.

According to one embodiment, a CT scanner is used to supply the projection images.

Finally, one may use a CT or MR scanner and segment the coronary arteries in 3D from a volumetric data sets to determine centerline and cross sections although operation does not rely by necessity on volumetric image data.

In a preferred embodiment exactly two angiographic images A1, A2 are received, preferably but not necessarily acquired at orthogonal projection directions and the following embodiment will be explained with reference to those two images although it is understood that in alternative embodiments (as outlined above) a single image is used or in yet other embodiments more than two images are used, such as three or four images.

At any rate, whatever the imaging modality, for present purposes the number of projection images input should allow computing to sufficient degree of approximation the local cross sectional areas of the vessel tree at the region of interest. In other words, if there is only a single image used, the computations involved herein (and as explained in more detail below) will be inherently approximate and will ultimately rely on reasonable assumptions as the extension of the vessel along the dimension not recorded in the signal imagery.

However, when dealing with vessels, it is reasonable to assume a circular or at least elliptical cross-sections, so two images are in general sufficient to estimate the minor and major axis to estimate cross-sectional area with sufficient detail for present purposes.

The proposed system is capable of delivering satisfactory results when receiving, as input, projection imagery acquired merely at a few discrete "sample" projection directions around the region of interest. Volumetric (that is, reconstructed CT image data) is not necessary but their use is envisaged herein in alternative embodiments.

Operation

In one non-limiting embodiment, two images A1, A2 are received at input port IN.

Images A1, A2 are then passed on to segmenter SEG. Segmenter SEG operates to segment the two images for the vessel tree footprint in each view. In one embodiment, the whole of the vessel tree is segmented although in other embodiments only a region of interest defined by a radius (ROI radius) around the actual stenosis stricture is segmented which in general is easy to identify. The ROI radius around the stenosed site is in one embodiment adjustable and extends to at about 2 to 5 cm to either side of the stenosis but this is merely a non-limiting example and other ROI radius definitions may be used with benefit in other use scenarios.

Image coordinates of the segmented vessel footprint in said ROI are then passed on to partitioner PAR. Partitioner PAR then proceeds along the segmented vessel tree portions to partition same into sections at a step width which in embodiment is set at about 5 to 10 mm. The step width is user adjustable in some embodiments. Because the geometry of the imager during the image acquisition is known, the required step width can be translated into pixel units on which Partitioner PAR then operates to define, for each input image A1, A2, a plurality of image portions hereinafter referred to as "vessel tree segments" j. Each vessel tree segment j records in the respective projection view certain geometric parameters that define the local geometry of the corresponding vessel tree section. In one embodiment, the geometric parameters include any one of the following (or any combination thereof): a portion of the vessel's centreline, the vessel's local cross sectional area A, the local centreline curvature κ, the vessel segment's length l, the local vessel perimeter P and the local vessel radius r.

The vessel tree segments j of each image A1 A2 are then passed on to adapter ADP. Adapter ADP is communicatively coupled to a database DB where a library of "basis" function $h_e(f)$ are held. Each basis function corresponds to a template of a local transfer function. Each transfer function defines a dedicated fluid dynamic model for a specific physical effect that would cause a change in fluid dynamic behavior. More particularly, and in one embodiment, each local effect transfer function in the library describes a certain pressure drop Δp caused solely by one specific physical effect, given a flow rate f and a certain local geometry of a given tubular structure of interest.

The individual templates of the local effect transfer functions $h_e(f)$ are modeled as odd polynomials with degree d:

$$h_e(f) = \alpha_e \, \text{sign}(f) |f|^d \quad (1)$$

The functions are templates in the sense that they include a parameterization denoted as the local geometry coefficient $\alpha_e$ associated with the respective effect e. Up to, in some cases, certain fluid properties of the blood, the local geometry coefficient $\alpha_e$ depends solely on the local vessel geometry, i.e., on the segmented outline or lumen of the vessel and its centreline as captured by each of the vessel tree segmentations j from which the coefficient can be computed. The signum function sign(f) denotes the direction ("+"/"−") of flow f.

The table in FIG. 6 includes, in terms of the local geometry coefficient $\alpha_e$, examples of different local effect transfer function templates as held in the library DB according to one embodiment.

In the table, the local geometry parameters A, κ, l, P and r are as previously defined and ρ and μ denote properties of the fluid of interest. In one embodiments, ρ and μ denote physiological parameters, in particular, blood density and blood viscosity, respectively.

The database holds lumped parameter models that are used for the simulation of the human blood circulation as described in more detail herein. In other words, the table in FIG. 6 summarizes how the respective local transfer function templates can be adapted to the local geometry of the vessel (as represented by the local geometry coefficient $\alpha_e$) in order to account singly, that is, in isolation, for a respective one of the pressure effects as named in the leftmost column. For instance, the first row describes how a pressure drop that is caused solely by the Bernoulli effect can be modeled. That is, if the vessel has locally, at a vessel section a "dumbbell" shaped local geometry as shown in the rightmost column, and if there was only the Bernoulli effect as the sole cause for pressure change, then said pressure change can be computed for said vessel section from equation (1) after adapting same to the local geometry parameters $A_{in}$, $A_{out}$.

But the local pressure drop is in general caused by more than one effect. Therefore, in order to enhance the fidelity of the FFR simulation as proposed herein, adapter ADP operates to compute for each vessel tree segment j pair (from the two images A1, A2) not only one local effect transfer function for a certain effect, but computes a dedicated local transfer function for each effect at that segment j. It will be understood that in general not each section j will attract a non-zero local effect transfer function contribution for each effect e. For instance, a relatively straight vessel segment will return an essentially zero contribution for the Borda-Carnot expansion effect. The same is done for each vessel section j as recorded in the pair of images A1, A2. The output is, for each vessel tree segment j, a plurality of local effect transfer functions, one function for a different effect. In other words, for each vessel tree segment j, different effect dependent coefficients $\alpha_{e,j}$ are computed. After processing all of the vessel tree sections j in this manner, the coefficients $\alpha_{e,j}$ that belong to the same effect can be summed across the vessel tree sections j to compute an overall, global (that is, for the whole vessel or vessel ROI) coefficient $\alpha_e = \Sigma_j \alpha_{e,j}$ for the respective effect. Using the global coefficients as constructed by this summation allows formulating the global effect transfer functions as per (1) for each effect for the whole vessel or vessel ROI. The upshot is that information on the individual, local, effect specific pressure drops from each vessel section j are consolidated into the respective global effect transfer functions $h_e(f) = \Sigma_j \alpha_{e,j} \, \text{sign}(f)|f|^d$ as per equation (1).

Figure 3:
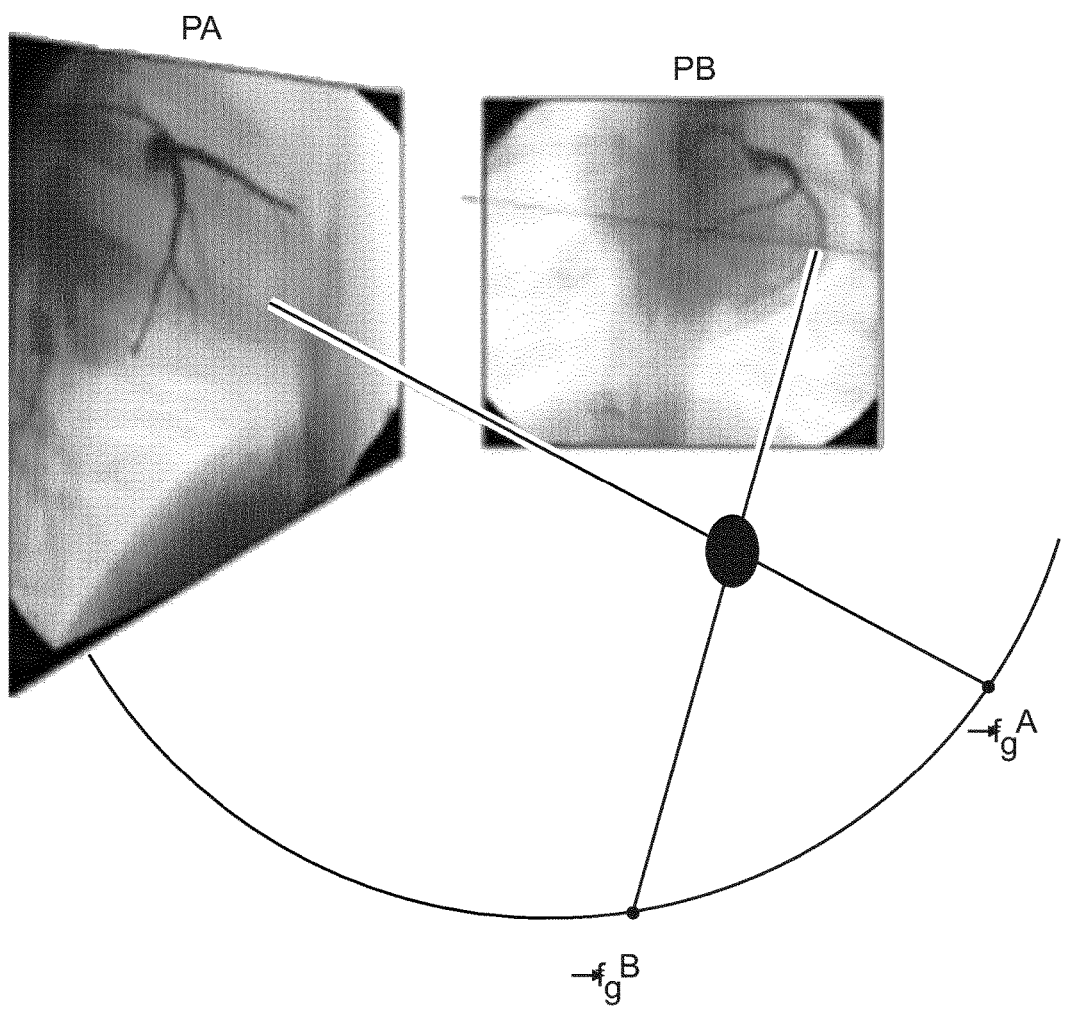
FIG. 3 shows an epipolar geometric estimation of a 3-D centerline point.

The local coefficients can be computed as per table of FIG. 6 from the local geometry parameters, as recorded in the vessel tree segments j. For instance, adapter ADP may be configured to use coronary artery modeling techniques to determine the Poiseuille friction coefficient $\alpha_P$ and the curvature effect coefficients $\alpha_C$. More specifically, both coefficients can be determined based on a 3D vessel centreline modeled from the two A1, A2 (or more projections) using the epipolar acquisition geometry as shown in FIG. 3, where $\vec{f}_g^{A1}, \vec{f}_g^{A2}$ denote the respective focal spot positions of in the imager's X-ray source XR when acquiring the two projection images A1, A2. Because the geometric relationship between the two projections A, A2 are known, a 3D centerline point can be determined as illustrated in FIG. 3. The centreline in each image A1, A2 can be constructed pointwise in this epipolar geometric manner. The spatial information on the focal spot positions can be retrieved from DICOM metadata in header of the images or can be otherwise retrieved from a record of the imager's geometry during the acquisition.

All other effects can be calculated based on at least two radii determined from corresponding vessel positions in the two angiographic projection images A1, A2. In other words, the underlying vessel geometry can be summarized by cross-sectional areas CSA taken along the 3D vessel centerline. Thus, in order to calculate these effects, it is not required to generate a full volume data set (voxel data set) or a 3D surface model of the vessel. The minimum requirement is the determination of a 3D centreline from two or more projection and knowledge of the acquisition geometry. To sum up, using the 3D centreline and the acquisition geometry, for one 3D point on the centreline the corresponding vessels and vessel radii can be determined on the related projections and the relevant geometric parameters like A, P, or r as per the table of FIG. 6 can be determined.

Figure 2A:
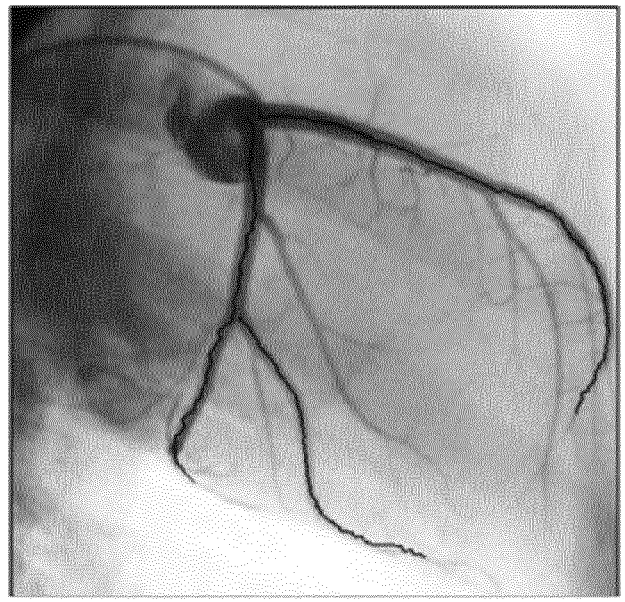
FIGS. 2A, B show projection views of the human vasculature illustrating a vessel centerline and cross sectional area estimates.
Figure 2B:
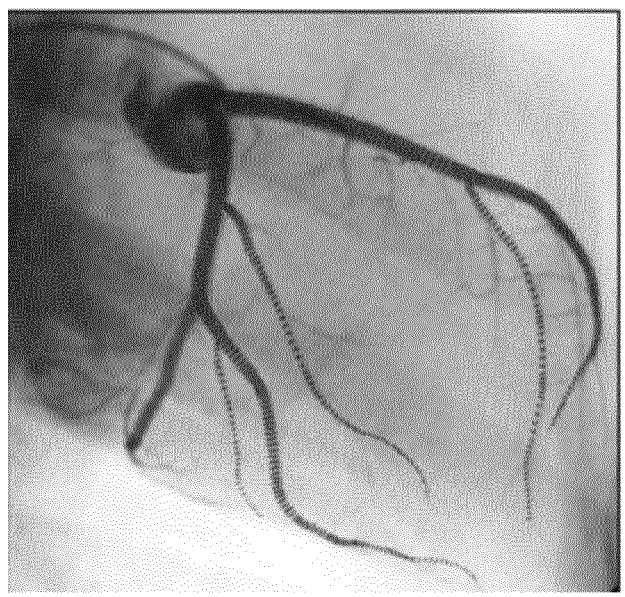

FIG. 2A illustrates A1 or A2 as an angiographic projection showing the vessel centerline in bold. FIG. 2B illustrates A1 or A2 as an angiographic projection showing local vessel radii taken across the centerline. The in-image measurements of the geometric parameters can be based on grey value thresholding. As can be seen in FIG. 2B for the example of the centerline, the geometrical parameters are in general derived from the collective image information as recorded in the corresponding tree section pair j in the two projections A1,A2.

Returning now to the process flow in the proposed image processing system IPS in FIG. 1, the plurality of global effect transfer functions (that is, one for each effect e) is then passed on to combiner Σ to form a composite transfer function $\Delta p=\Sigma_e w_e h_e(f)$ by linear combination of the various global effect transfer functions. This allows formulating a simplified model to calculate fluid behavior in the vessel ROI around the stenosis. The pressure drop Δp over the stenotic vessel segment at a given volumetric flow rate f is now modeled as a weighted sum of the different global pressure drop effects $h_e(f)$ to now accounting for pressure changes due to any one of the following or any combination thereof: i) Bernoulli's principle, ii) pressure losses due to friction caused by vessel ovality and/or curvature and or/or change of cross section geometry such as expansions and constrictions.

The weights $w_e$ are retrieved from the (or a different) database DB when forming the composite transfer function. In one embodiment, the effect weights are previously computed by training module TR in a learning phase through a statistical training learning procedure. In particular, given a set of examples $f_i$, $\Delta p_i$ of volumetric flow rates and pressure drops along with the vessel tree's geometry, the fitting of the weights is implemented in one embodiment as a least squares fitting, a regularized least squares fitting or a non-negative least squares fitting where the weight vector $w=[w_e]_e$ is found by minimizing a loss function similar to $w=\arg\min_w \Sigma_i (\Delta p_i - \Sigma_e w_e h_e(f_i))^2$, wherein i denotes an index for the samples and e is an index that denotes the respective effects e one wishes to account for in the training phase. For instance, using the library as per FIG. 6, the effects are as indicated therein and e=5 it being understood that the FIG. 6 library is merely one embodiment and different effects may be used in other embodiments. It is assumed herein that the training samples not only include the measurements $f_i$, $\Delta p_i$ but also corresponding geometric parameters such as A, r (as defined above) etc. that describe at least the local geometry for the respective measurements $f_i$, $\Delta p_i$.

The training samples can either be obtained by CFD simulations or by simultaneous pressure/flow or pressure/velocity measurements. As proposed herein the weights are adaptively chosen to account for interactions, interdependencies and correlations between the different effects e. This is very much unlike previous approaches, where the effects are examined separately in isolation whereas the method as implemented herein aims at inferring the interactions between the various pressure loss effects from an existing data corpus.

Once the composite transfer function is gotten and adapted to the vessel tree of the patient at hand, an evaluator EVAL can then compute different FFR values for any given pair $p_0$, f as per:

$$FFR = \frac{p_0 - \Delta p(f)}{p_0} = 1 - \frac{\Delta p(f)}{p_0} \quad (2)$$

In other words, the distal pressure $p_0$ behind the stenosis is divided by the proximal pressure before the stenosed site. The FFR value depends on both, the proximal pressure and the amount of flow through the stenotic region. The so computed FFR value(s) is (are) then output at an output port (not shown) for storage and/or can be otherwise processed.

The FFR equation (2) defines a 2D surface in where FFR depends on the two unknowns $p_0$, f. In one embodiment evaluator EVAL operates to sample the FFR surface as per (2) to produce a range of different FFR values by varying the flow and/or the proximal pressure each within physiologically reasonable intervals.

Figure 4:
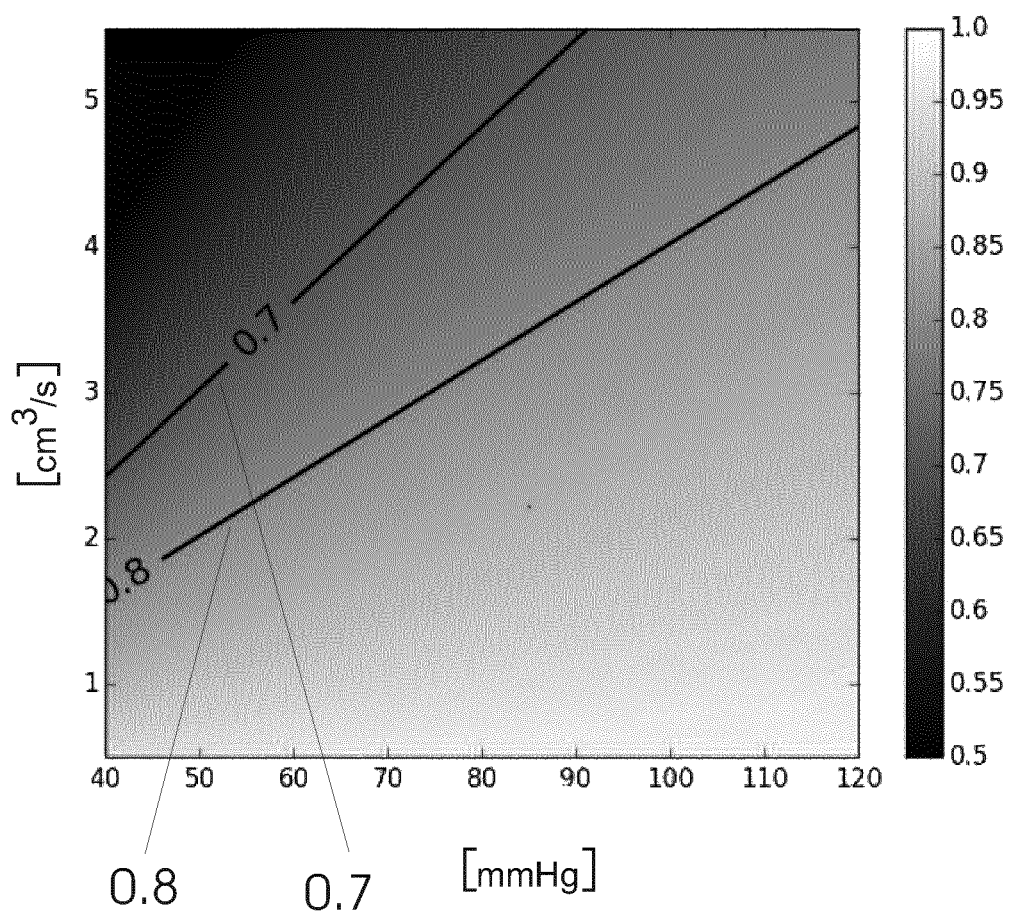
FIG. 4 shows a graphics display for displaying a range of FFR values.

In one embodiment, the plurality of data triples <$p_0$,f, FFR($p_0$, f)> as output by evaluator EVAL is then passed on to visualizer VS. In one embodiment visualizer VS operates to form a graphics display by mapping the sampled surface <$p_0$,f, FFR($p_0$, f)> onto a plane and the magnitude of the FFR values are color- or grey value encoded according to a user definable palette. The graphics display GD is then rendered for display on the monitor MT by driving the systems video card as controlled by the visualizer's VS output. FIG. 4 shows one embodiment of such a graphics display. The graphical rendering of the sampled FFR surface allows the physician to better assess the stenosis' severity by presenting the FFR as a function of the proximal pressure and the volumetric flow rate. In case a measurement of the proximal blood pressure is available, the 2D graphics display can be collapsed into a 1D curve. This proximal blood pressure value can be estimated from a catheter based measurement of the pressure in the aorta or from external blood pressure measurements (arm cuff). The color coding indicates the stenosis severity at a particular working regime. If the image acquisition is based on angiography, the catheter through with the contrast agent has or being administered can be used to obtain the measurement of the proximal pressure. It is not necessary (although this still can be done) to used dedicated pressure measurement catheters ("pressure wires").

Similarly, one can visualize FFR dependence on other quantities that are part of the computation but may not be known exactly such as hematocrit, blood viscosity, blood density.

Also—since CSA estimation from multiple 2D images is inherently approximate—one can also visualize the introduced effect of the CSA estimation on the FFR value. The user can then switch between those plots or combine and aggregate them into 3D plots. In other words, the visualizer allows the user to examine the uncertainty that attaches to the FFR value by "freezing" or holding constant certain user selectable values in equations (1),(2), and then let one or more of the remaining values vary in a user definable error interval. For instance, the user may be presented with a user interface with a listing of all variables. The user then clicks or otherwise specifies those variables which he wishes to hold constant. The remaining variables are then varied in respective error margins and the resulting FFR values are displayed in dependence on those variations. For instance when varying the CSA estimations A, the user can specify in one embodiment at which vessel tree segmentations j the variation is to be applied. In a simpler embodiment however the fixed error estimate is applied to all CSA estimations across all vessel tree segmentation sections j.

Clinical studies have shown that FFR values below 0.75 or 0.8 are critical in that they are an indication for a stenosis severity warranting intervention. It is then proposed in one embodiment to superimpose on the graphics display as per FIG. 1 contour lines at the critical 0.8 FFR value. However the 0.8 (or any other suitably suggestive threshold value) contour line is but one embodiment and should not be construed herein as limiting. In other contexts contour lines at different values may be called for instead.

In an alternative embodiment, it is not the FFR value itself that is displayed in the 2D or 3D plot but the area or volume of FFR values above or below the 0.8 threshold for the given vessel geometry in the calculated plot. This allows condensing the available information into a single number.

Although in the embodiment in respect of the adapter ADP as explained above in connection with FIG. 1, all effects are considered for each vessel tree section j, it should be appreciated that this is but one embodiment only. In an alternative embodiment it is only a sub-selection of local effect transfer functions as held in database that are applied to the vessel tree segmentation sections. For instance, in one embodiment it is the user who can decide which one of the effects they wish to consider at the various sections j. In one embodiment the user is presented with a graphical user interface that includes graphical symbols similar to the rightmost column in the table of FIG. 6, showing suggestive symbology for the various local geometries. The user can then click or otherwise specify which ones of the local effect transfer function are to be considered by the system when computing the local transfer functions.

Figure 5:
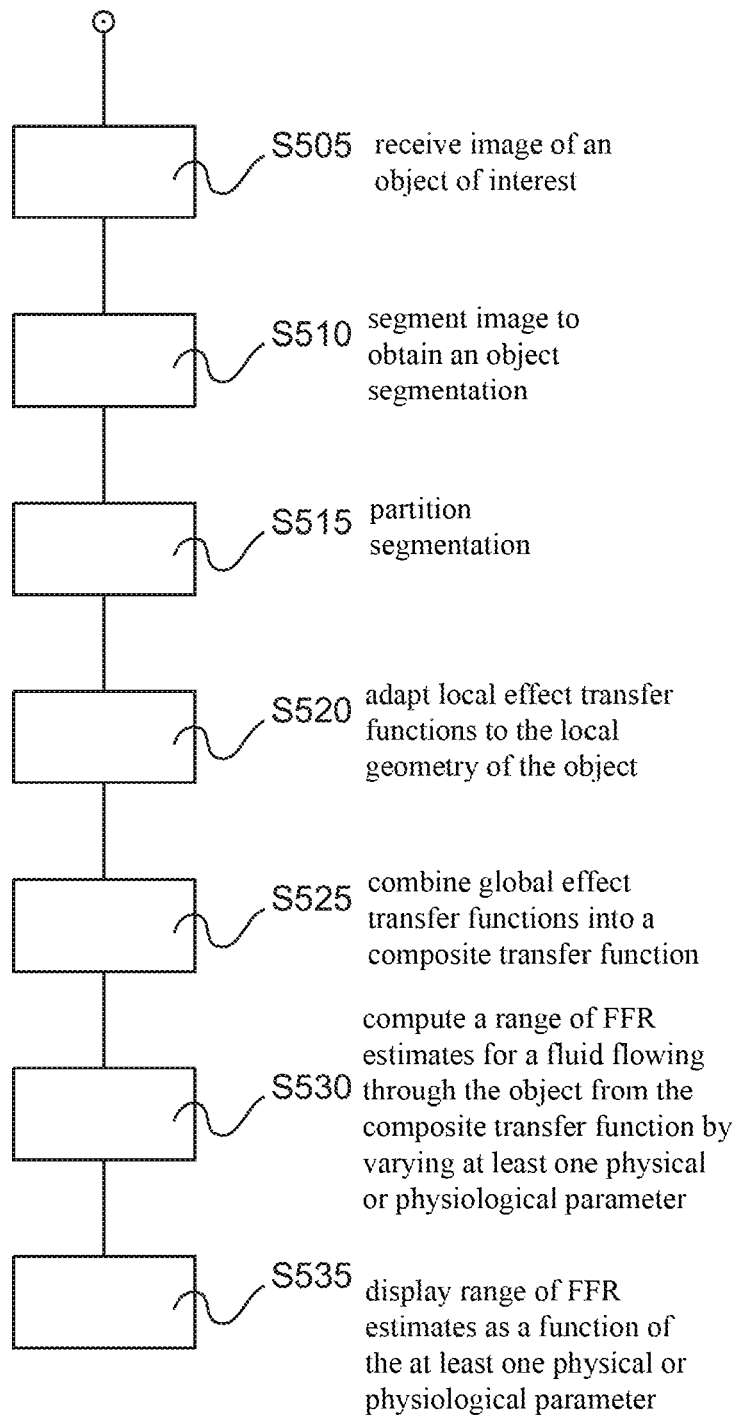
FIG. 5 shows a flowchart of an image processing method.

With reference to FIG. 5, there is shown a flow chart of an image processing method.

At step S505 at least one image including a projection view of an object of interest is received. In one embodiment the object of interest is a part of the human or animal cardiac vasculature.

At step S510 the image is segmented for the object's footprint as captured in the projection view to obtain an object segmentation such as a vessel tree segmentation. In one embodiment the segmentation is restricted to a region of interest centered around a stenosed site.

At step S515 the segmentation is partitioned into image components j. In one embodiment, the components are sections along the vessel tree in within the ROI.

At step S520 one or more (in one embodiment each) of a plurality of local effect transfer functions is adapted to the local geometry of the object as recorded in respective ones of the components j to obtain a plurality of global effect transfer functions $h_e$.

At step S525 the plurality of global effect transfer functions is combined into a composite transfer function for the object.

At step S530 an FFR estimate for a fluid flowing through the object is computed from the composite transfer function. In one embodiment, the computation step includes computing a range of FFR estimates by varying at least one physical or physiological parameter.

At step S535 the range of FFR estimates is displayed as a function of the at least one physical or physiological parameter.

In one embodiment, the components of image processing system IPS as per FIG. 1 all run on a single computing system. In an alternative embodiment an at least partly distributed architecture is likewise envisaged herein where one or more of the components are located remotely and are connected with each other and/or with the image processor IPS in a suitable communication network.

In one embodiment, image processing IPS (or at least some its components) is arranged as a dedicated FPGA or as a hardwired (standalone) chip.

In an alternate embodiment, image processing IPS or at least some of its components are resident in a work station of the imager IM The components of image processing system IPS may be programmed in a suitable scientific computing platform such as Matlab® and may be translated into C++ or C routines suitable to run on a computing system (such as the imager's workstation),In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   an input port for receiving at least one image including a projection view of an object of interest;
   a segmenter configured to segment the image to obtain an object segmentation for the object as per the projection view;
   a partitioner configured to partition the segmentation into components;
   an adaptation unit configured to adapt at least one of a plurality of local effect transfer functions to a local geometry of the object as recorded in respective ones of the components to obtain a plurality of global effect transfer functions;
   a combiner configured to combine the plurality of global effect transfer functions into a composite transfer function for the object;
   an evaluator configured to compute from the composite transfer function a fractional flow reserve (FFR) estimate for a fluid flowing through the object, wherein the evaluator operates to compute a range of FFR estimates by varying physical and physiological parameters;
   a visualizer configured to render for display on a display unit the range of FFR estimates as a function of at least one the physical and physiological parameters; and
   the display unit operating to display the range of FFR estimates in their functional dependence,
   wherein the physical and physiological parameters include at least one of pressure and flow rate, and wherein the range of FFR estimates is displayed as a function of the at least one of pressure and flow rate.

2. The image processing system of claim 1, wherein the physical and physiological parameters include is at least one of a hematocrit, a blood viscosity, and a blood density.

3. The image processing system of claim 1, wherein the local transfer functions are linearly combined based on weights previously learned from pressure versus flow rate sample measurements.

4. The image processing system of claim 1, wherein the image is acquired by one of a planar X-ray apparatus of the C-arm type and a rotational C-arm system.

5. An image processing method, comprising acts of:
   receiving at input port of an image processing (IPS) system at least one image including a projection view of an object of interest;
   segmenting the image by a segmenter of the IPS system to obtain an object segmentation for the object as per the projection view;
   partitioning by a partitioner of the IPS system the segmentation into components;
   adapting at least one of a plurality of local effect transfer functions to the local geometry of the object as recorded in respective ones of the components to obtain a plurality of global effect transfer functions;
   combining by a combiner of the IPS system the plurality of global effect transfer functions into a composite transfer function for the object;
   from the composite transfer function, computing by an evaluator of the IPS system a fractional flow reserve (FFR) estimate for a fluid flowing through the object including computing a range of FFR estimates by varying physical and physiological parameter, wherein the physical and physiological parameters include at least one of a pressure and a flow rate, and wherein the range of FFR estimates is displayed as a function of the at least one of the pressure and the flow rate; and
   displaying the range of FFR estimates as a function of the at least one of pressure and flow rate.

6. A non-transitory computer readable medium comprising computer instructions for performing an image processing method which, when executed by a processor, cause the processor to perform acts of:
   causing reception at an input port of an image processing (IPS) system at least one image including a projection view of an object of interest;
   segmenting the image by a segmenter of the IPS system to obtain an object segmentation for the object as per the projection view;
   partitioning by a partitioner of the IPS system the segmentation into components;
   adapting at least one of a plurality of local effect transfer functions to the local geometry of the object as recorded in respective ones of the components to obtain a plurality of global effect transfer functions;
   combining by a combiner of the IPS system the plurality of global effect transfer functions into a composite transfer function for the object; and
   from the composite transfer function, computing by an evaluator of the IPS system a fractional flow reserve (FFR) estimate for a fluid flowing through the object including computing a range of FFR estimates by varying physical and physiological parameter, wherein the physical and physiological parameters include at least one of a pressure and a flow rate, and wherein the range of FFR estimates is displayed as a function of the at least one of the pressure and the flow rate; and
   causing display of the range of FFR estimates as a function of the at least one of pressure and flow rate.

7. An image processing (IPS) system, comprising a processor, wherein the processor is programmed to perform acts of:
   causing reception at an input port of the IPS system at least one image including a projection view of an object of interest;
   segmenting the image by a segmenter of the IPS system to obtain an object segmentation for the object as per the projection view;
   partitioning by a partitioner of the IPS system the segmentation into components;
   adapting at least one of a plurality of local effect transfer functions to the local geometry of the object as recorded in respective ones of the components to obtain a plurality of global effect transfer functions;
   combining by a combiner of the IPS system the plurality of global effect transfer functions into a composite transfer function for the object; and
   from the composite transfer function, computing by an evaluator of the IPS system a fractional flow reserve (FFR) estimate for a fluid flowing through the object including computing a range of FFR estimates by varying physical and physiological parameter, wherein the physical and physiological parameters include at least one of a pressure and a flow rate, and wherein the range of FFR estimates is displayed as a function of the at least one of the pressure and the flow rate; and causing display of the range of FFR estimates as a function of the at least one of pressure and flow rate.

8. The IPS system of claim 7, wherein the processor is linearly combines the local transfer functions based on weights previously learned from pressure versus flow rate sample measurements.

* * * * *